(12) United States Patent
Neuhann et al.

(10) Patent No.: US 10,849,736 B2
(45) Date of Patent: Dec. 1, 2020

(54) EYE IMPLANT AND METHOD FOR MANUFACTURING SAME

(71) Applicant: MIRO GMBH, Munich (DE)

(72) Inventors: Thomas Neuhann, Munich (DE); Wolfgang G. Mueller-Lierheim, Munich (DE)

(73) Assignee: MIRO GMBH, Munich (DE)

( * ) Notice: Subject to any disclaimer, the term of this patent is extended or adjusted under 35 U.S.C. 154(b) by 0 days.

(21) Appl. No.: 15/315,663

(22) PCT Filed: Jun. 2, 2014

(86) PCT No.: PCT/EP2014/061391
§ 371 (c)(1),
(2) Date: Dec. 1, 2016

(87) PCT Pub. No.: WO2015/185099
PCT Pub. Date: Dec. 10, 2015

(65) Prior Publication Data
US 2017/0105835 A1    Apr. 20, 2017

(51) Int. Cl.
*A61F 2/16* (2006.01)
*G01M 11/02* (2006.01)

(52) U.S. Cl.
CPC .......... *A61F 2/1613* (2013.01); *A61F 2/1602* (2013.01); *G01M 11/025* (2013.01); *A61F 2/1621* (2013.01); *A61F 2/1637* (2013.01); *A61F 2240/001* (2013.01)

(58) Field of Classification Search
None
See application file for complete search history.

(56) References Cited

U.S. PATENT DOCUMENTS 6,215,096 B1    4/2001   Von Wallfeld et al.
2010/0274234 A1*  10/2010  Liang ............... A61F 9/008
                                              606/5

FOREIGN PATENT DOCUMENTS

| DE | 20 2008 004 608 U1 | 5/2008 |
| EP | 1 074 214 A1 | 2/2001 |
| EP | 0 954 255 B1 | 7/2002 |
| EP | 1 424 049 A1 | 6/2004 |
| EP | 2 365 379 A1 | 9/2011 |
| WO | WO-2006/060477 A2 | 6/2006 |
| WO | WO-2007 062864 A2 | 6/2007 |
| WO | WO-2009 124767 A1 | 10/2009 |

OTHER PUBLICATIONS

International Search Report and English Translation dated Feb. 13, 2015 in International Patent Application No. PCT/EP2014/061391.

* cited by examiner

*Primary Examiner* — David H Willse
*Assistant Examiner* — Javier G Blanco
(74) *Attorney, Agent, or Firm* — Squire Patton Boggs (US) LLP

(57) ABSTRACT

An eye implant with an optical implant region for correcting an imaging error of the eye. Biometrically determined data of optically effective components located in front of the retina of the eye is obtained through wave front measurement. The optical implant region is adjusted, based on the biometrically determined data, for a monofocal vision with a visual acuity of at least 0.7 (70%) within a field of focus depth of at least 2 diopters.

8 Claims, 2 Drawing Sheets

EYE IMPLANT AND METHOD FOR MANUFACTURING SAME

CROSS-REFERENCE TO RELATED APPLICATIONS

This application is the U.S. National Stage of International Patent Application No. PCT/EP2014/061391, filed on Jun. 2, 2014. The entire contents of the foregoing application is incorporated herein by reference in its entirety.

BACKGROUND

The invention relates to an eye implant having an optical lens implant region which corrects imaging errors in the eye, as well as a method for production of same.

The optical system of the eye primarily involves the cornea as the light-receiving lens, the iris forming a diaphragm with variable diameter (pupil), and the lens of the eye. The viewing direction of the eye is determined by six muscles. The eye can adapt its imaging system to the brightness of the surrounding area by changing, among other things, the diameter of the pupil. The lens is attached via fibers (ciliary zonules) to a ring muscle. The contraction of this ring muscle causes the zonule fibers to relax and thus causes a stronger curvature of the lens surface, thereby resulting in a reduction of the focal distance of the lens. As a result, images in the near distance instead of images in the far distance are projected sharper onto the retina. This type of process is referred to as accommodation. The ability of the iris to change the pupil diameter, as well as the elasticity, and thus the accommodation ability of the lens, decrease with increasing age.

The established methods used in ophthalmology, optometry and ophthalmic optics for improving the vision above all deal with the correction of errors in the optical system of the eye. To be mentioned in particular are eye glasses, contact lenses, refractive-surgical interventions for changing the cornea curvature, so-called intraocular contact lenses (ICL) implanted into the anterior chamber of the eye, intraocular lenses (IOL) implanted after the removal of the natural lens, as well as additional lenses implanted between the iris and the natural lens or the intraocular lens.

Spherical, rotation-symmetrical lenses and refractive cornea interventions are used to correct the average focal distance of the eye. With spherical lenses as with the eye, light rays close to the center of the bundle of rays are deflected differently than light rays far from the center. This deviation is also called spherical aberration. It can be corrected through aspherical (rotation ellipsoid) optical surfaces. In praxis, several correction approaches are used for this: correction only of the spherical aberration of the lens used or the operatively changed cornea; correction of the spherical aberration of the lens used in combination with the average spherical aberration of the human eye known from the literature, as well as individual correction of the system for a specific patient eye and the lens used, respectively the correction of the cornea.

The human eye is not precisely rotation symmetrical. When significant deviations occur, this is referred to as astigmatism. The astigmatism is corrected with toric lenses (cylindrical lenses), respectively a toric change of the shape of the cornea.

However, even aspheric-toric lenses do not take into account all errors of the optical system of the eye. The surfaces of cornea and lens contain non-symmetrical irregularities. In addition, the cornea apex, the pupil center, the lens apex and the point of most acute vision on the retina (fovea) are generally not located on the same axis. Rather, the eye is oriented such that the object to be viewed precisely is imaged on the point of most acute vision (favea), regardless of therewith connected additional optical errors of the eye. The patent document EP 0 954 255 B1, respectively U.S. Pat. No. 6,215,096 B1 describe a method for computing optics by means of which it is possible to achieve a sharp projection of images on the retina of the human eye.

With ideal imaging, the actual resolution of the retina is delimited by the refraction of the light. Two spatially separate points can still be distinguished if the maximum light-intensity of the second point is located in the first refraction minimum of the first point. With a 4 mm pupil opening and 600 mm wavelength of the light, this corresponds to a distance of approximately 4 µm on the retina. The diameter of the receptors at the location of most acute vision on the retina (fovea) is approximately 1 to 3 µm. Among other things this means that even with an ideal imaging of the human eye, an imaged striped pattern can never cause moiré effects.

The accommodation ability of the eye, meaning the ability to vary the focal point by changing the lens curvature, continuously declines following the human birth. With normal eyesight for a 45-year old, objects at a distance of less than 40 cm therefore generally are no longer imaged sharply on the retina. This is remedied either with reading glasses, multi-focal or varifocal glasses or a bifocal contact lens. With multi-focal glasses, varifocal glasses and bifocal contact lenses, the line of vision determines the focal distance of the visual aid. The removal of the clouded eye lens (cataract) with subsequent implantation of an intraocular lens also results in the loss of the accommodation ability of the eye. In that case, so-called accommodating intraocular lenses are used at times, but with little success so far. In addition, bifocal or trifocal intraocular lenses are implanted in 1 to 2 percent of cases, for which the optics have diffractively or refractively two or three focal distances. With these intraocular lenses, the patient always sees sharp and non-sharp images simultaneously on the retina. The total amount of light in each focus is not available either for the near distance or the far distance.

SUMMARY

The object of the present invention is to create an implant for implanting in the eye which leads to a sharp vision in the near and far distance, taking into consideration the signal processing in the eye which follows the imaging.

This object is solved according to the invention with the features of patent claim 1. The dependent claims disclose further improvements of the invention.

The eye implant according to the invention can be used as intraocular lens, either to replace the natural eye lens or to replace a previously implanted artificial lens. The eye implant can also be used in addition to the natural lens which remains in the eye, in order to correct imaging errors. The eye implant can furthermore be implanted in addition to an intraocular lens which replaces the natural eye lens.

The eye implant according to the invention has an optical implant region that corrects an imaging error of the eye and, starting with biometrically ascertained data of optically effective components positioned in front of the retina and, if applicable, the eye lens remaining in the eye or an artificial lens and its axial position, or data obtained through wave front measurements, is adjusted for monofocal vision with a visual acuity of at least 0.7 (70%), preferably at least 0.8 (80%) within a depth of field of at least two diopters, preferably at least 3 diopters.

The above-listed visual acuity values refer to the photoptic vision (day vision, cone vision) with physiological pupil width having at least a diameter of 3 mm.

The eye implant has advantageously proven to be robust with respect to expected production tolerances and deviations in the precise positioning in the eye, as well as intra-operative and post-operative changes to be expected in the eye, in particular on the cornea. The imaging characteristics of the optical implant region, adjusted for an optimum imaging, advantageously ensure the desired visual acuity in case of deviations of the seating of the implant in the eye from the pre-computed position in the range of a rotational angle of up to 2.5°, preferably up to 5°, around the line of vision axis (z-axis) and in the range of rotational angles of up to 1.5°, preferably up to 3°, around the thereto perpendicular lateral axes (x-axis; y-axis). The imaging characteristics of the optical implant region, adjusted for an optimum imaging, also ensure advantageously the desired visual acuity in case of deviations of the implant seat in the eye from the pre-computed position in the range of a displacement of up to ±0.1 mm, preferably ±0.2 mm, in the direction of the line of vision axis and in the range of displacements of up to ±0.2 mm, preferably up to ±04 mm, in the direction of the thereto perpendicular lateral axes. Especially preferred is that the imaging characteristics of the optical implant region, adjusted for an optimum imaging, ensure the desired visual acuity in case of deviations of the implant seating from the pre-computed position in the complete "area of deviation," spanned by the above-specified rotation and displacement deviation values.

When producing the eye implant according to the invention, the signal processing in the neuronal vision system that follows the optical imaging on the retina is taken into consideration.

The process of seeing involves the following steps:
a) The imaging of images from the surrounding area with the aid of the optical eye system on the retina of the eye;
b) The conversion of optical stimuli hitting the receptors of the retina to neuronal signals of the ganglion cells (nerve cells) in the retina;
c) The further transmission of the visual signal from the ganglion cells by the vision nerve (axons of the ganglion cells) to the side protuberances (corpora geniculata) and the processing of the neuronal signals therein, as well as the further transmission of the signals to the primary visual cortex of the brain and the further processing therein;
d) The further transmission of the signals to the secondary visual cortex and the cerebrum, as well as the analysis of these signals in the secondary visual cortex and the cerebrum.

The retina contains two types of light receptors, namely approximately 120 million rods and approximately 6 million cones. The rods are responsible for detecting weak light signals. The cones are responsible for the high spatial resolution of objects and the color detection. Three different types of cones are available for this which differ in the wavelength of the light-absorption maximum. The highest density of cones is in the point of most acute vision on the retina (fovea centralis; depression with a diameter of approximately 1.5 mm in the center of the macula lutea or yellow spot). The highest density of rods is in the peripheral area of the fovea centralis.

The approximately 126 million light receptors transmit their signals to only about 1 million ganglion cells (nerve cells), the nerve fibers (neuronal fibers; axons) of which form the visual nerve (nervus opticus). Of the 1 million axons approximately 10 percent go to the colliculus superior and serve to control eye movement, pupil size and lens accommodation while the remaining 90 percent go to the side geniculate bodies of the thalamus (corpus geniculatum laterale, CGL) and serve the visual cognition.

Nerve cells (neurons) are composed of cell bodies (soma), neuronal fibers (axons) with branching and treeing (dendrites). Each neuron can receive signals (nerve pulses, neuronal pulses) from many preceding neurons and can transmit these further to many following neurons. The neuronal signals are electrical pulses in the range of approximately 100 millivolt, based on chemical processes. The neuron discharges ('fires') in an all-or-nothing process. The stimulus amplitude is converted to frequency and regularity of the nerve pulses. Following each pulse, the neuron needs at least 1 to 2 milliseconds for recovery, meaning the maximum 'firing rate' is 500 to 800 pulses per second. Even without stimulus, the neurons fire at a low rate (spontaneous rate). The stimulus amplitude is therefore delimited by the maximum firing rate and the spontaneous rate.

The pulse is transmitted by the cell body (soma) of the neuron to the axon. The axon end section is located near the dendrites or the cell body of a following neuron, but is spatially separated by a gap (synapse). The pulse is transmitted through release of a chemical substance (neuro transmitter) by the pre-synaptic neuron. Neuro transmitters attach themselves to the cell membrane of the post-synaptic neuron. Depending on the type of neuro transmitter and the post-synaptic cell membrane, the pre-synaptic pulse can have a stimulating (increase in the firing rate) or inhibiting (reduction in the firing rate) effect on the post-synaptic neuron. Each neuron generally receives stimulating and inhibiting pulses from several other neurons which in sum increase, reduce or keep the same their own pulse rate as compared to the spontaneous rate.

Regarding the interaction of neurons, a simple distinction must be made between linear switching, convergence switching and convergence switching with side (lateral) inhibition. With the linear switching, there is precisely one synapse between a receptor neuron and the forwarding neuron, and the signal generated in the receptor neuron is passed on only to this one forwarding neuron. All synapses are stimulating, which means a linear passing on of the signal without processing. For the convergence switching, several receptor neurons with their axons converge to the next plane and the one following it, wherein all synapses are stimulating. This results in an increase in the detection of weak signals, wherein simultaneously the local resolution decreases, for example on the retina. For the convergence switching with lateral inhibition, the receptor neurons converge to the next higher level for neurons while, at the same time, the synapses of side neurons are inhibiting on the next higher level. This results in maximum stimulation if the stimulus has a specific spatial expansion ('ON region') and results in inhibition for the further spatial expansion ('OFF region'). With reference to the retina, the convergence switching with lateral inhibition among other things forms the basis for the 'image acuity' which already starts on the retinal level. In the retina, the connectivity between receptors (cones and rods) and the passing-on ganglionic cells occurs linear, convergent and convergent with lateral inhibition through bipolar, horizontal and amacrine cells. The convergence switching of the rods is responsible for the high light sensitivity whereas the ganglionic cells 'fire' only when stimulated simultaneously by several rods. The cones in the fovea centralis are connected linear to the ganglionic cells, which contributes to a higher local resolution. The retina region on which a single neuron of a higher level responds is referred to as receptive field for this neuron.

The optical imaging quality of the average human eye is relatively poor. The surfaces of cornea and lens have asymmetrical irregularities. In addition, the cornea apex (apex), the pupil center, the lens apex and the point of most acute vision on the retina (fovea centralis) as a rule are not located on the same axis. Nevertheless, the eye orients itself so that the object to be viewed closely is imaged on the point of most acute vision (fovea), regardless of additional optical errors of the eye, connected therewith. The optical imaging of a point therefore occurs as a spot of irregular size in the eye, depending on the non-completeness of the individual optical apparatus. The fact that the eye still perceives sharp images is thanks to its ability for 'image sharpening' (lateral contrast processing), which starts in particular in the retina.

A sharp point in the environment is therefore imaged as a spot on the retina, as light-intensity distribution via a plurality of receptors, owing to the imaging function of the eye. It is only the neuronal image sharpening which leads to the perception of a sharp point.

The human eye has a field of focus depth of approximately 0.75 diopters, even at a high age. Since the natural eye lens does not accommodate at that age, this 'field of focus depth' is presumably thanks to the above-explained neuronal image sharpening ability of the eye.

The invention uses the previously explained image sharpening abilities of the eye through lateral signal processing in the retina to achieve an optimum field of focus depth with the aid of an eye implant that images monofocal, wherein an acute vision of objects at different distances is achieved. The principle according to the invention consists of the optical imaging already being optimized in such a way that the lateral contrast processing capacity of the visual system, primarily the retina, is needed only to a minimum degree for correcting the imaging errors in the focus and is therefore available to a high degree for sharpening the non-sharp vision caused by defocusing and can be used to increase the natural field of focus depth.

BRIEF DESCRIPTION OF THE DRAWINGS

The invention is now explained further with the aid of the Figures, which show in.

DETAILED DESCRIPTION

Figure 1:
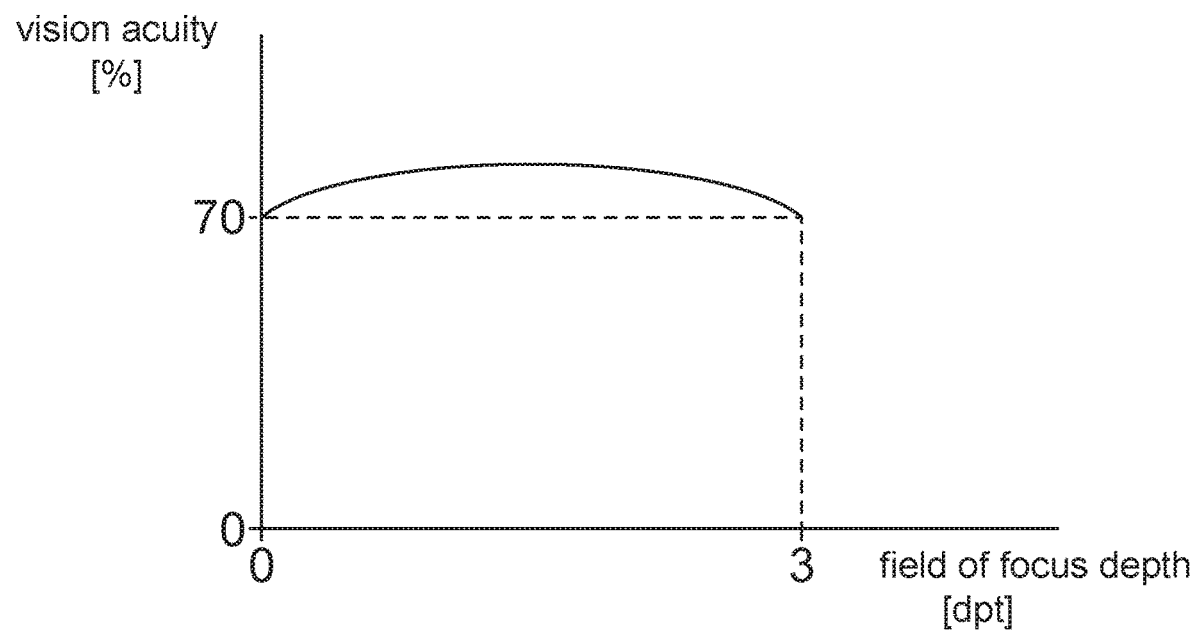
FIG. 1 An exemplary representation of the visual acuity achieved with an eye implant according to one embodiment of the invention, within a specific field of focus depth.

FIG. 1 shows the visual acuity achieved with an eye implant according to one embodiment of the invention, within a specific field of focus depth, in this case 3 diopters. This visual acuity is (0 diopters) for the distance vision and (3 diopters) 0.7 (70%) for the near vision. The visual acuity refers to the ability of the eye with optimum correction through the eye implant to perceive two object points separately. This is possible if in the fovea centralis of the retina, the cone located between two stimulated cones is not stimulated more than 70%. The grid size in this case is 2 μm.

Figure 2:
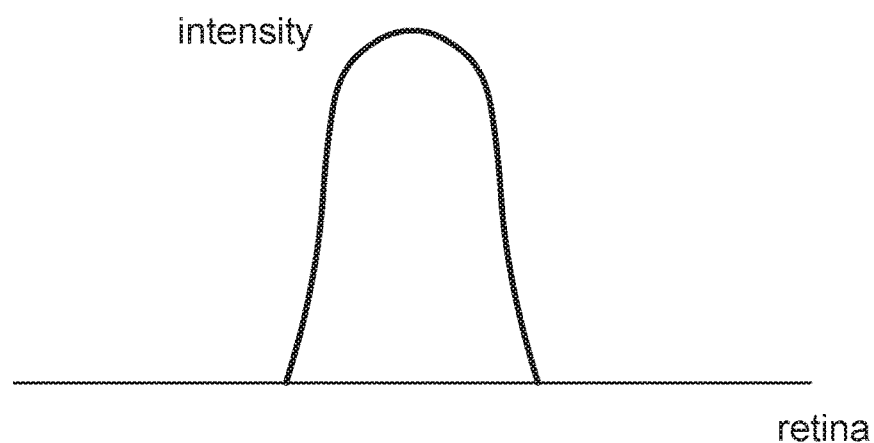
FIG. 2 An example of the light-intensity distribution of the image generated on the retina of the eye, according to the embodiment.

FIG. 2 shows the light intensity distribution of the image projected by the eye implant onto the retina of the eye which causes a lateral signal processing on the retina, making it possible to achieve an optimum field of focus depth with a visual acuity of at least 0.7 (70%) for the distance vision and the near vision.

Prior to the implantation, the eye is measured biometrically (topography of front and back surfaces of the cornea; axial length of the eyeball and, with phakic implants and intraocular implants, the position and topography of the front and back surfaces of the implant). The surface topography as the desired topography for the implant to be implanted into the eye is computed from these measuring values in combination with the planned position for the eye implant and the refractive index of the material. The data required for computing the optical implant region can furthermore be determined through a wave front measurement of the imaging components, in particular for additional lenses to be implanted in phakic or pseudo-phakic eyes.

The front eye section is preferably examined to determine the characteristics of the refractive components of the eye. Suitable for this is a "Scheimpflug" camera, for example, which can be used to take sectional images of the anterior eye chamber in a non-contacting way. These pictures permit an analysis of the complete cornea, the anterior chamber and the natural lens. In the process, geometric data such as central radii, cornea sphericity, different curvatures of the cornea, chamber angle, chamber volume and height of the anterior chamber as well as the lens clouding can be analyzed. Such an analysis of the front eye section is known, for example, from EP 1074214 B1.

The position of the implant in the eye can advantageously also be predicted based on the analysis data.

A desired topography for one of the two implant surfaces or both implant surfaces can be computed based on the data obtained through analysis and the known refractive indices, in particular the cornea and the aqueous humor of the eye, wherein the material used for the implant is also taken into consideration. This material refers to commercially available polymers, for example MMA/HEMA copolymers. A suitable material is also known, for example, from WO 2007/062864.

However, the implant can be produced from any implantable material having optical quality.

Standard methods are used for producing the optic for the eye implant, in particular the individual implantable lens, wherein one of the optic surfaces can have a standard geometry (spherical, aspherical or toric) and can be produced through turning, molding or injection compression molding. The second optic surface is preferably produced with a programmable lathe or through irradiation with a laser, in particular post-processing with a laser, suitable for creating free-form surfaces, wherein operational steps are preferred which dispense with a subsequent polishing of the surface. The production through direct molding with correspondingly formed molding tools is also possible.

Based on the desired topography, machine data are computed which are suitable for controlling the processing of a standard blank surface by mechanical machining or laser post-processing. In dependence on these machine data, the machining of the standard blank surface then takes place, for example in a suitable lathe or milling machine. A lathe or milling machine is preferably used that permits processing of the surface with such precision that a subsequent polishing is not necessary, wherein a diamond tool is advantageously used for this in the lathe. The standard blank for producing the implant, in particular the individual intraocular lens, through machining or laser processing is advantageously a blank produced through injection compression molding. In this way, a blank is obtained with precisely specified dimensions for the surface, which dimensions serve as starting point for producing the desired topography through machining or laser processing.

When using the process of injection compression molding, the haptic used to secure the implant in the eye can also be molded on.

The quality control of the topography of the optics designed as free-form surfaces preferably involves analyzing the measured and in particular the reflected wave front, wherein the desired surface is selected as mathematical reference and deviations from the topography are computed by analyzing the measured wave front as compared to the expected wave front. The wave front is preferably measured at a wavelength where the non-reflected light is absorbed by the implant material, so as to minimize the super-imposition of the reflected wave front of the optic front surface through reflections of the back surface of the optic.

A wave front sensor embodied as Shack-Hartmann sensor, for example, can be used to measure the topography of the implant surface. The Shack-Hartmann sensor contains an arrangement of micro lenses with a local-resolution light sensor arranged in its focal plane, e.g. embodied as CCD sensor. The measured topography causes wave fronts which trigger a deflection of the focal points of the micro lens arrangement on the local resolution light sensor. Measuring results can thus be obtained for the topography created on the implant surface.

The measurement with the aid of the Shack-Hartmann sensor makes use of the transmitted light method, for which the light used for the measurement is radiated through the optical implant region. However, a measuring method using light reflected on the implant surface and detected by the Shack-Hartmann sensor can advantageously also be used. These measuring methods are known, for example, from DE 20 2008 004 608 A1 for detecting implant errors.

A topographic sensor that scans the surface of the optical implant region and is embodied as distance sensor or angle sensor can also be used for measuring the topography of the implant surface. A topographic sensor of this type is known, for example, from WO 2009/124767.

The measured topography of the optical implant region is compared to the desired topography. For this, the measuring results are converted to the format of the desired topography. However, it is also possible to adapt the desired topography to the format of the measured topography for a comparison.

On the implant, the desired topography can be produced on one of the two implant surfaces. However, it is also possible to produce the respective topographies on both implant surfaces (front and back surfaces of the eye implant) which are designed individually, in order to correct the defective vision resulting from the eye components.

Figure 3:
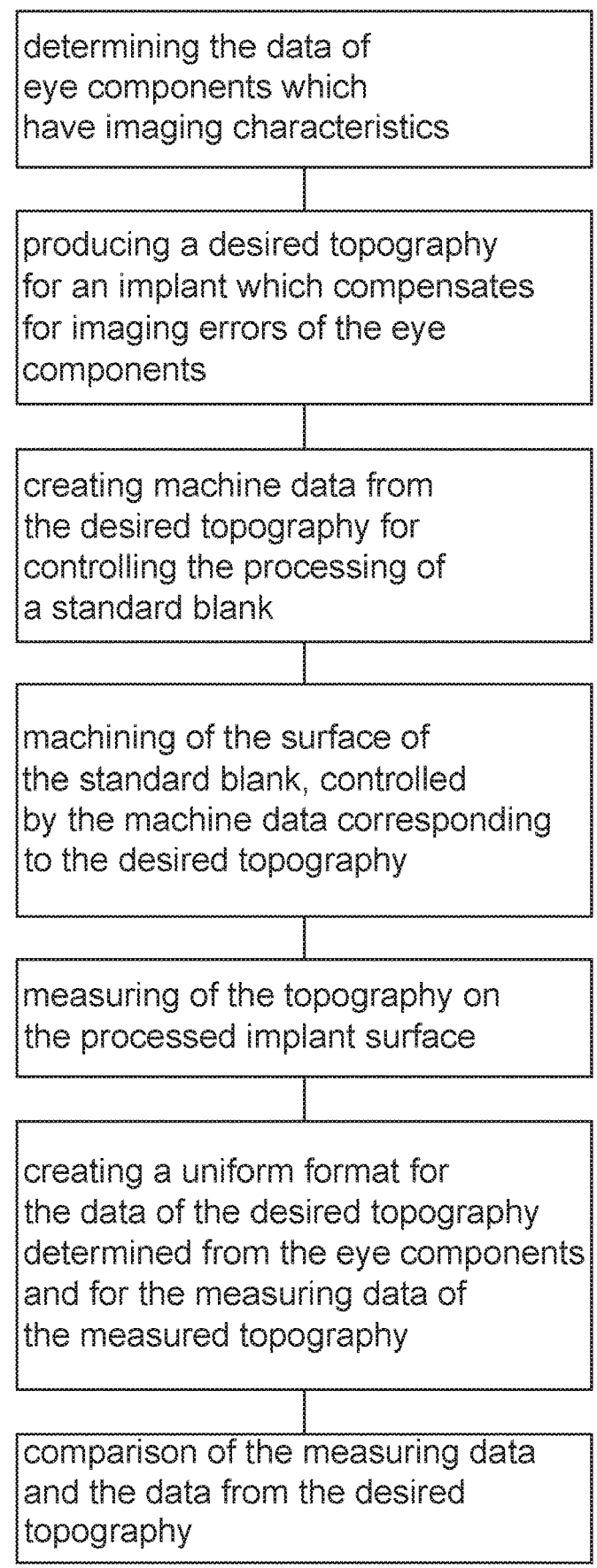
FIG. 3 An exemplary embodiment of the operational steps for producing the eye implant according to this embodiment, as shown with a flow chart.

The flow chart in the attached FIG. 3 shows the various steps for producing an eye implant, in particular an intraocular lens, according to one exemplary embodiment.

The invention claimed is:

1. An intraocular lens (IOL) comprising:
an optical implant region for correcting an imaging error of the eye,
wherein a surface topography of the optical implant region is adjusted based on biometrically determined data of optically effective components located in front of the retina of the eye and data obtained through wave front measurement so as to correct imaging deficiencies of the eye,
wherein the optical implant region is optimized in such a way that the lateral contrast processing capacity of the retina is needed only to a minimum degree for correcting the imaging errors in the focus and is therefore available to a high degree for sharpening the non-sharp vision caused by defocusing and to increase the natural depth of focus,
wherein, due to the corrected imaging deficiencies at the optical implant region, a lateral signal processing in the retina achieves an optimum monofocal vision with a visual acuity of at least 0.7 (70%) within a depth of focus of at least 2 diopters, and
wherein the biometrically determined data is obtained from at least two of the following optically effective components located in front of the retina of the eye: cornea, anterior chamber, natural crystalline lens, position of the natural crystalline lens, position of an artificial lens previously implanted to replace the natural crystalline lens, and axial length of the eye ball.

2. The intraocular lens according to claim 1, having a visual acuity of at least 0.8 (80%) within the depth of focus.

3. The intraocular lens according to claim 1, having a depth of focus of at least 3 diopters.

4. The intraocular lens according to claim 1, wherein adjusted imaging characteristics of the optical implant region ensure the desired visual acuity in case a position of the intraocular lens in the eye deviates from a pre-computed position, within a range of a rotational angle of up to 5°, around the line of a vision axis and in the range of rotational angles of up to 3°, around lateral axes which are perpendicular thereto.

5. The intraocular lens according to claim 1, wherein adjusted imaging characteristics of the optical implant region ensure the desired visual acuity in case a position of the intraocular lens in the eye deviates from a pre-computed position within a range of a displacement of up to +0.2 mm, in the direction of the line of a vision axis and in the range of displacements of up to +0.4 mm, in the direction of lateral axes which are perpendicular thereto.

6. The intraocular lens according to claim 1, wherein the optical implant region is sized and configured for generating the highest light intensity for an image projected onto the retina.

7. The intraocular lens according to claim 1, wherein the surface topography of the optical implant region is formed on a front surface that faces the cornea of the eye and on a back surface that faces the retina of the eye.

8. The intraocular lens according to claim 1, wherein the intraocular lens is configured for replacing the natural eye lens, or as a lens that can be implanted in addition to an implant replacing the natural eye lens, or as replacement for an implant replacing the natural eye lens.

* * * * *